(12) United States Patent
Wilkes et al.

(10) Patent No.: US 8,444,611 B2
(45) Date of Patent: May 21, 2013

(54) NEGATIVE PRESSURE WOUND TREATMENT DRESSING

(75) Inventors: Robert P. Wilkes, San Antonio, TX (US); Teryl Blane Sanders, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 511 days.

(21) Appl. No.: 10/895,700

(22) Filed: Jul. 21, 2004

(65) Prior Publication Data

US 2005/0020955 A1    Jan. 27, 2005

Related U.S. Application Data

(60) Provisional application No. 60/489,344, filed on Jul. 22, 2003.

(51) Int. Cl.
*A61F 13/00* (2006.01)
*A61F 13/06* (2006.01)

(52) U.S. Cl.
USPC ............ 604/305; 604/308; 604/304; 602/42; 602/41

(58) Field of Classification Search
USPC ............... 604/289, 304–5, 307–8; 602/41–52
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,376,868 A | 4/1968 | Mondiadis |
| 3,520,300 A | 7/1970 | Flower |
| 3,568,675 A | 3/1971 | Harvey |

(Continued)

FOREIGN PATENT DOCUMENTS

| | | |
|---|---|---|
| AU | 550575 A1 | 8/1982 |
| AU | 745271 | 3/2002 |

(Continued)

OTHER PUBLICATIONS

Merriam OnLine definitions—"occlusive", "occlude" and "occluding".*

(Continued)

*Primary Examiner* — Susan Su (57) ABSTRACT

A wound treatment dressing for applying negative pressure wound therapy to a wound on an extremity, such as on the heel of a foot. The dressing includes a fluid manifold positioned within a fenestrated drape to form a contoured occlusive wrapping. A contoured porous pad is placed adjacent or within the wound, and is covered by the occlusive wrapping. Flexible tubing is attached to or through a port to allow fluid communication of negative pressure to the contoured pad from a source of negative pressure. The negative pressure is communicated from the source, through the tube, through the fluid manifold, and through the fenestrations of the occlusive wrapping, to the wound. The fluid manifold conducts the negative pressure from a position away from the wound site to the contoured pad at the wound site.

8 Claims, 6 Drawing Sheets

U.S. PATENT DOCUMENTS

| | | | |
|---|---|---|---|
| 3,648,692 A | 3/1972 | Wheeler | |
| 3,682,180 A | 8/1972 | McFarlane | |
| 3,742,952 A | 7/1973 | Magers et al. | |
| 3,763,857 A * | 10/1973 | Schrading | 128/853 |
| 3,774,611 A | 11/1973 | Tussey et al. | |
| 3,779,243 A | 12/1973 | Tussey et al. | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez | |
| 4,141,361 A | 2/1979 | Snyder | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vailancourt | |
| 4,529,402 A | 7/1985 | Weilbacher et al. | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,652 A | 5/1987 | Weilbacher | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,841,962 A | 6/1989 | Berg et al. | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,981,474 A | 1/1991 | Bopp et al. | |
| 4,985,019 A | 1/1991 | Michelson | |
| 5,000,164 A | 3/1991 | Cooper | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,112,323 A | 5/1992 | Winkler et al. | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,215,539 A * | 6/1993 | Schoolman | 604/541 |
| 5,232,453 A | 8/1993 | Plass et al. | |
| 5,261,893 A * | 11/1993 | Zamierowski | 604/180 |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,329 A | 8/1994 | Croquevielle | |
| 5,342,376 A | 8/1994 | Ruff | |
| 5,344,415 A | 9/1994 | Debusk et al. | |
| 5,358,494 A | 10/1994 | Svedman | |
| 5,437,622 A | 8/1995 | Carion | |
| 5,437,651 A | 8/1995 | Todd et al. | |
| 5,449,379 A * | 9/1995 | Hadtke | 607/107 |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,688,225 A | 11/1997 | Walker | |
| 5,784,811 A | 7/1998 | Mauch | |
| 5,809,665 A | 9/1998 | Suenaga | |
| 5,913,838 A | 6/1999 | Reilly | |
| 6,071,267 A | 6/2000 | Zamierowski | |
| 6,129,692 A | 10/2000 | Mathis | |
| 6,135,116 A | 10/2000 | Vogel et al. | |
| 6,174,306 B1 | 1/2001 | Fleischmann | |
| 6,178,662 B1 | 1/2001 | Legatzke | |
| 6,241,747 B1 | 6/2001 | Ruff | |
| 6,287,316 B1 | 9/2001 | Agarwal et al. | |
| 6,290,685 B1 * | 9/2001 | Insley et al. | 604/317 |
| 6,345,623 B1 * | 2/2002 | Heaton et al. | 128/897 |
| 6,360,457 B1 | 3/2002 | Qui et al. | |
| 6,361,512 B1 | 3/2002 | Mackay et al. | |
| 6,425,194 B1 | 7/2002 | Brie | |
| 6,471,685 B1 * | 10/2002 | Johnson | 604/890.1 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,626,891 B2 | 9/2003 | Ohmstede | |
| 6,631,568 B2 | 10/2003 | Howlett et al. | |
| 6,663,610 B1 * | 12/2003 | Thompson et al. | 604/313 |
| 6,685,681 B2 | 2/2004 | Lockwood et al. | |
| 6,695,824 B2 * | 2/2004 | Howard et al. | 604/305 |
| 6,736,787 B1 | 5/2004 | McEwen et al. | |
| 6,752,794 B2 | 6/2004 | Lockwood et al. | |
| 6,814,079 B2 | 11/2004 | Heaton et al. | |
| 6,855,135 B2 * | 2/2005 | Lockwood et al. | 604/313 |
| 6,979,324 B2 | 12/2005 | Byordi et al. | |
| 7,070,584 B2 * | 7/2006 | Johnson et al. | 604/313 |
| 7,207,977 B2 * | 4/2007 | Thompson et al. | 604/313 |
| 7,279,612 B1 * | 10/2007 | Heaton et al. | 602/42 |
| 7,282,038 B2 * | 10/2007 | Gillis et al. | 601/151 |
| 2001/0000262 A1 | 4/2001 | McEwen et al. | |
| 2001/0031943 A1 * | 10/2001 | Urie | 604/43 |
| 2001/0043943 A1 | 11/2001 | Coffey | |
| 2002/0017304 A1 | 2/2002 | Heaton et al. | |
| 2002/0065494 A1 | 5/2002 | Lockwood et al. | |
| 2002/0077661 A1 | 6/2002 | Saadat | |
| 2002/0082567 A1 | 6/2002 | Lockwood et al. | |
| 2002/0115951 A1 | 8/2002 | Norstream et al. | |
| 2002/0115952 A1 * | 8/2002 | Johnson et al. | 602/41 |
| 2002/0120185 A1 | 8/2002 | Johnson | |
| 2002/0143286 A1 | 10/2002 | Tumey | |
| 2002/0150720 A1 * | 10/2002 | Howard et al. | 428/131 |
| 2002/0178499 A1 * | 12/2002 | Augustine et al. | 5/423 |
| 2002/0198504 A1 | 12/2002 | Risk, Jr. et al. | |
| 2003/0050594 A1 * | 3/2003 | Zamierowski | 604/46 |
| 2003/0061733 A1 | 4/2003 | Karsten | |
| 2003/0125649 A1 | 7/2003 | McIntosh et al. | |
| 2003/0176828 A1 * | 9/2003 | Buckman et al. | 602/48 |
| 2003/0216672 A1 | 11/2003 | Rastegar et al. | |
| 2004/0030304 A1 | 2/2004 | Hunt et al. | |
| 2004/0064132 A1 | 4/2004 | Boehringer et al. | |
| 2005/0004534 A1 | 1/2005 | Lockwood et al. | |
| 2005/0020955 A1 | 1/2005 | Sanders et al. | |
| 2005/0027218 A1 | 2/2005 | Filtvedt et al. | |
| 2005/0070858 A1 | 3/2005 | Lockwood et al. | |
| 2005/0101940 A1 * | 5/2005 | Radl et al. | 604/543 |
| 2005/0137539 A1 | 6/2005 | Biggie et al. | |
| 2005/0228329 A1 * | 10/2005 | Boehringer et al. | 602/52 |
| 2005/0261642 A1 | 11/2005 | Weston | |

| | | | |
|---|---|---|---|
| 2005/0261643 | A1 | 11/2005 | Bybordi et al. |
| 2006/0100556 | A1 | 5/2006 | Hargens et al. |
| 2006/0100586 | A1 | 5/2006 | Karpowicz et al. |
| 2006/0149171 | A1 | 7/2006 | Vogel et al. |
| 2006/0155260 | A1* | 7/2006 | Blott et al. .............. 604/543 |
| 2006/0189909 | A1 | 8/2006 | Hurley et al. |
| 2006/0189910 | A1 | 8/2006 | Johnson et al. |
| 2006/0287621 | A1 | 12/2006 | Atkinson et al. |
| 2007/0027414 | A1 | 2/2007 | Hoffman et al. |
| 2007/0060848 | A1 | 3/2007 | Erdmann |
| 2007/0124959 | A1 | 6/2007 | Meffan |
| 2007/0167884 | A1 | 7/2007 | Mangrum et al. |
| 2007/0185426 | A1 | 8/2007 | Ambrosio et al. |
| 2007/0218101 | A1 | 9/2007 | Johnson et al. |
| 2007/0225663 | A1 | 9/2007 | Watt et al. |
| 2007/0265585 | A1 | 11/2007 | Joshi et al. |
| 2007/0265586 | A1 | 11/2007 | Joshi et al. |
| 2008/0047164 | A1 | 2/2008 | Vindriis |
| 2008/0066343 | A1 | 3/2008 | Sanabria-Hernandez |
| 2008/0071234 | A1 | 3/2008 | Kelch et al. |

FOREIGN PATENT DOCUMENTS

| | | | |
|---|---|---|---|
| AU | 755496 | | 12/2002 |
| CA | 2005436 | | 6/1990 |
| DE | 26 40 413 | A1 | 3/1978 |
| DE | 43 06 478 | A1 | 9/1994 |
| DE | 295 04 378 | U1 | 9/1995 |
| DE | 198 44 355 | A1 | 4/2000 |
| DE | 10 2004 055 702 | B3 | 11/2005 |
| EP | 0117632 | A2 | 1/1984 |
| EP | 0100148 | | 2/1984 |
| EP | 0161865 | | 11/1985 |
| EP | 0358 302 | | 3/1990 |
| EP | 1 018 967 | B1 | 8/2004 |
| EP | 1872763 | A1 | 1/2008 |
| GB | 692578 | | 6/1953 |
| GB | 2 195 255 | A | 4/1988 |
| GB | 2 197 789 | A | 6/1988 |
| GB | 2 220 357 | A | 1/1990 |
| GB | 2 235 877 | A | 3/1991 |
| GB | 2333965 | A | 8/1999 |
| GB | 2329127 | B | 8/2000 |
| GB | 2415908 | A | 1/2006 |
| SG | 71559 | | 4/2002 |
| WO | WO 80/02182 | | 10/1980 |
| WO | WO 87/04626 | | 8/1987 |
| WO | WO 88/01499 | A1 | 3/1988 |
| WO | WO 90/10424 | | 9/1990 |
| WO | WO 93/09727 | | 5/1993 |
| WO | WO/94/20041 | | 9/1994 |
| WO | WO 96/05873 | | 2/1996 |
| WO | WO 96/06559 | A1 | 3/1996 |
| WO | WO 97/18007 | | 5/1997 |
| WO | PCT/GB98/02713 | | 9/1998 |
| WO | WO 99/13793 | | 3/1999 |
| WO | WO 00/59424 | A1 | 10/2000 |
| WO | WO 00/64394 | A1 | 11/2000 |
| WO | WO-01/85248 | A1 | 11/2001 |
| WO | WO 01/89431 | A1 | 11/2001 |
| WO | WO 03/057307 | A1 | 7/2003 |
| WO | WO 03/099188 | A1 | 12/2003 |
| WO | WO 2004018020 | A1 * | 3/2004 |
| WO | WO 2005/123170 | A1 | 12/2005 |
| WO | WO 2007/092397 | A2 | 8/2007 |
| WO | WO 2007/133618 | A2 | 11/2007 |
| WO | WO 2008/036361 | A2 | 3/2008 |
| WO | WO 2008057600 | A2 | 5/2008 |
| WO | WO 2008/100440 | A1 | 8/2008 |
| WO | WO 2008/100446 | A2 | 8/2008 |

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery, vol. 38, No. 6, Jun. 1997, pp. 563-577; Lippincott Williams & Wilkins, Inc., Philadelphia, PA, U.S.A.

Susan Mendez-Eastman, RN; When Wounds Won't Heal, RN Jan. 1998, vol. 61(1); Medical Economics Company, Inc., Montvale, NJ, USA.

James H. Blackburn II, MD et al.; Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; Letter to the editor; British Journal of Plastic Surgery, 1998, vol. 51(3), p. 267: Elsevier Science/The British Assocition of Plastic Surgeons, United Kingdom.

S.E. Greer, et al.; The Use of Subatmospheric Pressure Dressing Therapy to Clos Lymphocutaneous Fistulas of the Groin; British Journal of Plastic Surgery (2000), 53, p. 484-487, Article No. BJPS2000.3360, Elsevier Sdence/The British Association of Plastic Surgeons, United Kingdom.

George V. Letsou, M.D., et al. .; Stimulation of Adenylate Cyclase Activity in Cultured Endothelial Cells Subjectied to Cyclic Stretch; Journal of Cardiovascular Surgery, 31, 1990, pp. 634-639; Edizonia Minerva Medica, Torino, Italy.

PCT International Search Report; PCT international application PCT/GB98/02713; Jun. 8, 1999.

PCT Written Opinion; PCT international application PCT/GB98/02713; Jun. 8, 1999.

PCT International Examination and Search Report, PCT international application PCT/GB96/02802; Jan. 15, 1998 and Apr. 29, 1997.

PCT Written Opinion, PCT international application PCT/GB/96/02802; Sep. 3, 1997.

International Search Report for PCT international application PCT/GB95/01983; Nov. 23, 1995.

Patent Abstract of Japan; JP4129536; Terumo Corporation; Apr. 30, 1992.

PCT International Search Report; PCT international application PCT/US04/23541; Feb. 18, 2005.

PCT Written Opinion, PCT international application PCT/US04/23541, Feb. 18, 2005.

Kostyuchenok, B.M, et al. ;Vacuum Treatment in the Surgical Management of Purulent Wounds; Vestnik Khirurgi, Sep. 1986.

Davydov, Yu. A., et al; Vacuum Therapy in the Treatment of Purulent Lactation Mastitis; Vestnik Khirurgi, Sep. 1986.

Yusupov, Yu. N., et al; Active Wound Drainage, Vestnik Khirurgi, vol. 138, Issue 4, 1987.

Davydov, Yu. A., et al; Bacteriological and Cytological Assessment of Vacuum Therapy of Purulent Wounds; Vestnik Khirurgi, Oct. 1988.

Davydov, Yu. A., et al; Concepts for the Clinical-Biological Management of the Wound Process in the Treatment of Purulent Wounds by Means of Vacuum Therapy; Vestnik Khirurgi.

Orringer, Jay, et al; "Management of Wounds in Patients with Complex Enterocutaneous Fistulas"; Surgery, Gynecology & Obstetrics, Jul. 1987, vol. 165, pp. 79-80.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Bjorn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96.

K.F. Jeter, T.E. Tintle, and M. Chariker, "Managing Draining Wounds and Fistulae: New and Established Methods,"*Chronic Wound Care*, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164.

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

European Search Report dated Feb. 7, 2008; European Application No. 04 778 864.1.

European Official Action dated Apr. 30, 2008; European Application No. 04 778 864.1.

New Zealand Examination Report dated Aug. 27, 2007; New Zealand Patent Application No. 544731.

Chinese Office Action mailed Sep. 4, 2008; Chinese Application No. 200480020083.5.

Chinese Office Action issue date Dec. 11, 2009; Chinese Application No. 200480020083.5.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. Therapy Clinical Guidelines, A reference source for clinicians, Jul. 2007.

Arcand, "Negative Pressure Wound Therapy and its Application to Orthopaedics. Part II: Clinical Application", Osteo Trauma Care 2006; 14:254-258.

Culliford, "A Novel Technique for Vacuum Assisted Closure Device Application in Noncontiguous Wounds", Journal of Plastic, Reconstructive & Aesthetic Surgery 2006.

Armstrong, "Plantar Pressure Changes Using a Novel Negative Pressure Wound Therapy Technique", Journal of the American Podiatric Medical Association, Sep./Oct. 2004, vol. 94. No. 5, pp. 456 460.

"Guidelines for Managing Pressure Ulcers with Negative Pressure Wound Therapy", a Supplement of Advances in Skin & Wound Care, vol. 17, Suppl. 2, Nov./Dec. 2004.

Venturi, "Mechanisms and Clinical Applications of the Vacuum-Assisted Closure (VAC) Device", Am J Clin Dermatol 2005: 6(3): 185-194.

Singapore Search and Written Opinion (issued by Austrian Patent Office) date mailed Aug. 5, 2009; Singapore Patent Application No. 200804990-0.

Response to non-final office action filed Aug. 26, 2010 for U.S. Appl. No. 12/006,566.

Non-Final Office Rejection date mailed Apr. 27, 2010 for U.S. Appl. No. 12/069,245.

Response filed Jul. 19, 2010 for U.S. Appl. No. 12/069,245.

Restriction Requirement date mailed Feb. 25, 2010 for U.S. Appl. No. 12/006,566.

Response to Restriction Requirement filed Mar. 25, 2010 for U.S. Appl. No. 12/006,566.

Non-Final Office Action date mailed May 27, 2010 for U.S. Appl. No. 12/006/566.

International Search Report and Written Opinion date mailed Feb. 19, 2009; PCT Application No. PCT/US2008/088635.

Lavery, Lawrence, et al: "Emerging Concepts with VAC Therapy"; vol. 20, Publication date Jul. 1, 2007, Issue No. 7.

Notice of Allowance date mailed Oct. 1, 2010 for U.S. Appl. No. 12/069,245.

Final Office Action date mailed Nov. 9, 2010 for U.S. Appl. No. 12/006,566.

\* cited by examiner

NEGATIVE PRESSURE WOUND TREATMENT DRESSING

This application claims the benefit under Title 35 U.S.C. §119(e) of U.S. Provisional Patent Application No. 60/489,344 filed under 37 C.F.R. 1.53(b)(2) on Jul. 22, 2003.

FIELD OF THE INVENTION

This invention relates to the treatment of open, chronic wounds, as well as burns and skin grafts. More specifically this invention relates to dressings for the treatment of wounds to the extremities, such as the heel of a human foot, by means of negative pressure wound therapy.

BACKGROUND OF THE INVENTION

Negative pressure wound therapy has been utilized for the treatment of open wounds and has been commercialized by Kinetic Concepts, Inc. of San Antonio, Tex., by its proprietary V.A.C.® product line. In practice, the application to a wound of negative gauge pressure, as commercialized by Kinetic Concepts, Inc. under the designation "VACUUM ASSISTED CLOSURE" (or "V.A.C.") therapy, typically involves the mechanical-like contraction of the wound with simultaneous removal of excess fluid, which is often accomplished by means of a polymer foam and occlusive drape dressing in fluid communication with a negative pressure source. In this manner, negative pressure wound therapy augments the body's natural inflammatory process while alleviating many of the known intrinsic side effects, such as the production of edema caused by increased blood flow absent the necessary vascular structure for proper venous return. As a result, negative pressure wound therapy has been highly successful in the promotion of wound closure, healing many wounds previously thought largely untreatable.

Many of these wounds include decubitus and venous stasis ulcers to the lower extremities, especially the foot. Closure of these wounds has been difficult and often times impossible using traditional techniques, such as skin grafting, sharp debridement, or combinations thereof. Failure to close these wounds, which have often been present for several years, can lead to necrotizing of the tissue, and in many cases amputation of the extremity. Use of negative pressure wound therapy has proven highly successful in closing these wounds. However, treatment of the lower extremities with negative pressure wound therapy, especially to wounds of the foot and heel can be difficult, especially considering the nature of the location of the wound. Particular concern arises with maintaining the dressing on the extremity, especially in light of the frequent movement of the foot, and friction often associated with foot coverings, including socks, stockings, and shoes. Of particular concern, is the ability to maintain a negative pressure at the wound site when the dressing is in place, as air leaks may occur during movement of the foot, which can adversely affect the therapy being administered.

For the foregoing reasons, there is a need for a negative pressure wound treatment dressing system that is capable of maintaining a negative pressure over an extremity that has heretofore been difficult to treat using traditional negative pressure wound therapy dressings. Additionally, there is a need for a negative pressure wound treatment dressing system that is capable of maintaining a negative pressure over a wound which exists in a highly contoured part of the body, or a portion of the body that undergoes frequent movement or friction against clothing or other outside forces.

It is therefore an object of the present invention to provide a negative pressure wound treatment dressing system that provides a means for maintaining a negative pressure over a contoured extremity, such as the foot, and more specifically the heel of the foot.

SUMMARY

In accordance with the foregoing objects, the present invention generally comprises a fenestrated and contoured occlusive wrapping having a fluid manifold, a receiving site, fluid communicator arms extending from the receiving site, and an occlusive drape enclosing the fluid manifold. The occlusive drape generally includes a wound facing inner drape and an outward facing outer drape, and an aperture substantially aligned with the receiving site. A concave porous pad is placed adjacent or within a wound on an extremity, such as the heel of a foot, and is covered by the occlusive drape. Flexible tubing may be attached to or through the aperture, so as to allow for fluid communication of negative pressure to the porous pad from a source of negative pressure connected to an opposite end of the flexible tubing. The negative gauge pressure is communicated from the source, through the tube, through the fluid manifold in the occlusive drape, and through fenestrations in the occlusive drape, such that negative gauge pressure is applied to the wound. The fluid manifold serves to conduct the negative pressure from a position away from the wound site to the contoured porous pad at the wound site. Such an arrangement allows for the tubing to connect to the occlusive drape of the present invention at a position least likely to be dislodged during normal ambulation of the patient.

Attachment means are formed on the outer edges of the occlusive drape to form an airtight seal over the wound. Such attachment means may be an adhesive coated on the occlusive drape for attachment to an intact area of tissue or skin. The adhesive is coated on the perimeter edge of the occlusive drape such that a pouch is formed when the occlusive drape is secured over the porous pad.

A collection canister is provided between the negative pressure source and the occlusive drape for collecting any effluents that may be drawn from the wound during application of negative pressure.

The tubing is connected to the occlusive wrapping and pad through an aperture in the outer layer of the wrapping, or through a flanged tubing connector as has been described in U.S. Pat. No. 6,345,623, entitled "Surgical drape and suction head for wound treatment," to Heaton, et al., the disclosure of which is incorporated herein by reference as though fully set forth. Alternative embodiments allow the tubing to be placed within or embedded in the fluid manifold.

The foregoing has outlined some of the more pertinent objects of the present invention. These objects should be construed to be merely illustrative of some of the more prominent features and applications of the invention. Many other beneficial results can be attained by applying the disclosed invention in a different manner or by modifying the invention as will be described. Accordingly, other objects and a fuller understanding of the invention may be had by referring to the following Detailed Description of the Invention, which includes the preferred embodiment.

BRIEF DESCRIPTION OF THE DRAWINGS

These and other features and advantages of the invention will now be described with reference to the drawings of certain preferred embodiments, which are intended to illustrate and not to limit the invention, and wherein like reference numbers refer to like components, and in which.

DETAILED DESCRIPTION

Although those of ordinary skill in the art will readily recognize many alternative embodiments, especially in light of the illustrations provided herein, this detailed description is exemplary of the preferred embodiment of the present invention as well as alternate embodiments, the scope of which is limited only by the claims that may be drawn hereto.

The details of the preferred embodiments of present invention are graphically and schematically illustrated in the accompanying drawings. Like elements in the drawings are represented by like numbers, and any similar elements are represented by like numbers with a different lower case suffix.

Figure 1A:
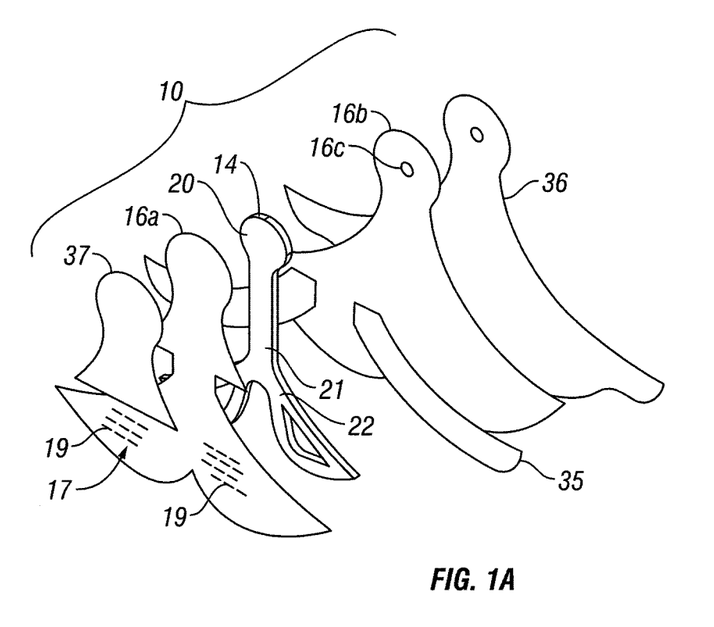
FIG. 1A, is an exploded view of the occlusive wrapping of the present invention.
Figure 1B:
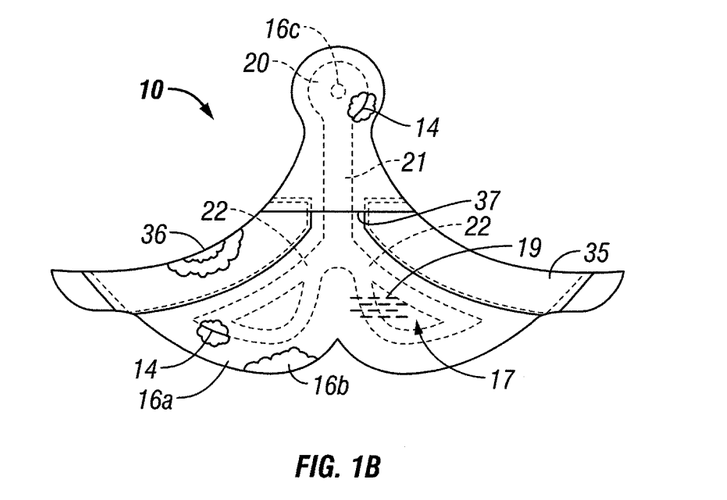
FIG. 1B is an orthogonal front view of the assembled occlusive wrapping of FIG. 1A, shown partly in section.

Referring now to FIGS. 1A and 1B in particular, there is illustrated the primary components of the occlusive wrapping 10 of the negative pressure dressing system that operates in accordance with the present invention. The occlusive wrapping 10 includes of a fluid manifold 14 enclosed within inner drape 16a and an outer drape 16b. Each of these drapes 16a and 16b are preferably made of a clear vapor permeable polyurethane material. The wound facing layer of inner drape 16a and the outward facing layer of outer drape 16b are sealed along their periphery to secure the fluid manifold 14 between the inner drape 16a and the outer drape 16b. Inner drape 16a includes fenestrations 19 in a wound contact region 17, so as to allow for fluid communication through the inner drape 16a to the fluid manifold 14. Outer drape 16b includes an aperture 16c substantially aligned with receiving site 20, through which tubing may fluidly communicate with the receiving site 20 of the fluid manifold 14, so as to allow for fluid communication of negative pressure to a porous pad from a source of negative pressure connected to an opposite end of the tubing (as shown in FIG. 4G). The fluid manifold 14 illustrated in FIG. 1A provides an extension region 21 and fluid communicator arms 22 that allows for attachment of a fluid communication port (not shown) at a position away from the wound site. The type of wounds desired to be treated by the present system are often situated at a position that has, at times, been difficult to maintain a reduced pressure using traditional negative pressure wound therapy techniques described herein. The occlusive wrapping 10 of the present invention overcomes this difficulty by communicating the negative pressure along the fluid manifold 14 of the occlusive wrapping 10. FIG. 1B shows essentially the same components of the occlusive wrapping 10 as shown in FIG. 1A. In this view of FIG. 1B from the wound side of the wrapping, wound contact region 17 on inner drape 16a (shown partly in section) is shown to be bordered by portions of outer drape 16b covered over with removable liner components 35, as well as second removable liner 37. Protective liner 36 (only minimally exposed in this view by partial section of inner drape 16a and outer drape 16b) supports outer drape 16b of occlusive wrapping 10.

Figure 2:
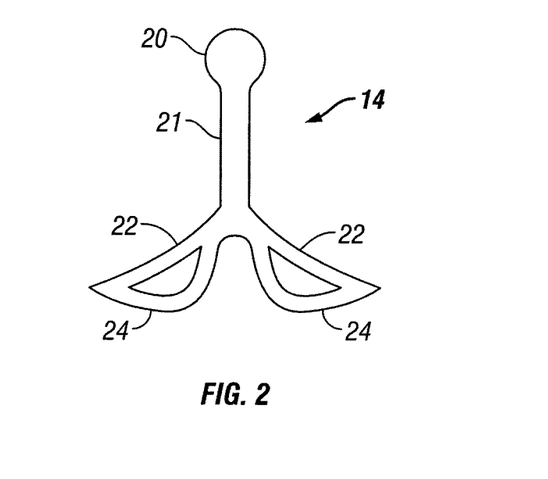
FIG. 2 is an orthogonal front view of a fluid manifold of FIG. 1A.

FIG. 2 illustrates the fluid manifold 14. As described above, the fluid communication port (not shown) of the overall system is adapted to be attached to a receiving site 20 of the manifold 14. The receiving site 20 is most preferably a circular shaped foam section of the manifold 14 that is approximately the size of the fluid communication port. Fluid communicator arms 22 extend distally from the receiving site 20 area of the fluid manifold 14 into the wound contact regions 17. In the embodiment illustrated in FIG. 2, the extension region 21 is interposed between the receiving site 20 and the fluid communicator arms. The fluid communicator arms 22 in a first embodiment terminate in loops 24, having openings for viewing the wound perimeter when, as in the preferred embodiment, inner and outer drapes 16a and 16b comprise a transparent material. In an alternative embodiment (not shown), fluid communicator arms 22 may terminate in fingers that extend distally from the fluid communicator arms 22 without forming loops.

Figure 3A:
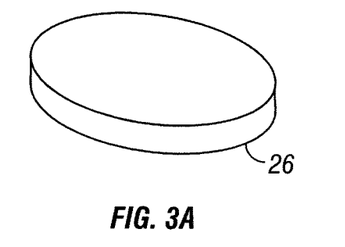
FIG. 3A is a perspective view of a contoured porous pad of the present invention.
Figure 3B:
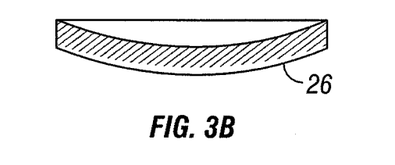
FIGS. 3B and 3C are cross-sectional views of the contoured porous pad of FIG. 3A taken along section lines 3B-3B and 3C-3C, respectively, in FIG. 3D.
Figure 3C:
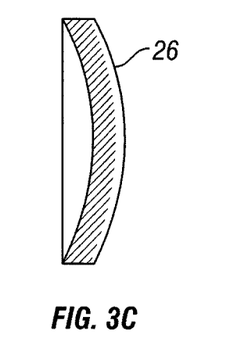
Figure 3D:
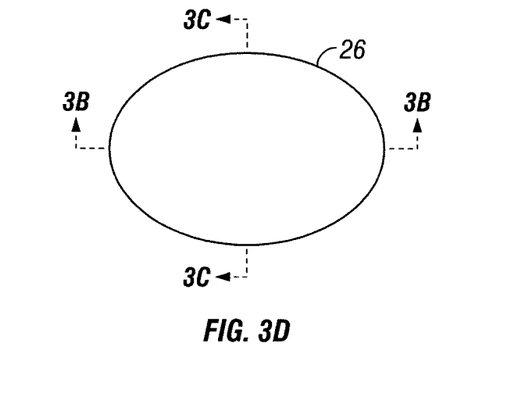
FIG. 3D is a top plan view of the contoured porous pad of FIG. 3A.

A contoured pad 26 as illustrated in FIGS. 3A-3D is utilized as a wound contact screen to prevent unwanted adhesions, direct fluid away from the wound through pores within the pad 26, and exert contracting forces on the wound margins as negative pressure is applied through the manifold 14 and to the pad 26. The contoured pad 26 and fluid manifold 14 of the occlusive wrapping 10 are preferably made of a porous polymer foam material, such as polyurethane or polyvinyl alcohol foam. The pad 26 is preferably constructed into an elliptical shape as illustrated in FIG. 3D, but may also be more symmetrically circular to accommodate more uniform wounds.

Figure 4A:
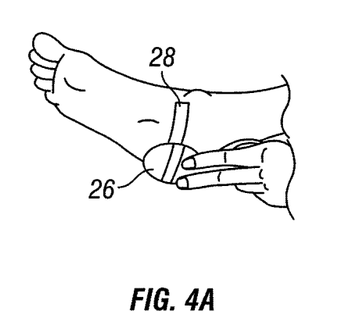
FIGS. 4A-4G are perspective views of the negative pressure wound treatment dressing system, illustrating the steps of applying the dressing system to a wound on the heel of a foot.
Figure 4B:
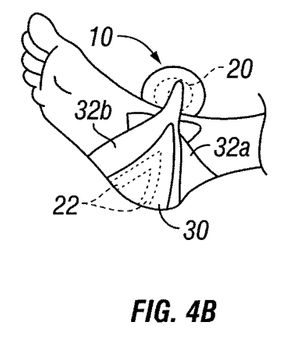
Figure 4C:
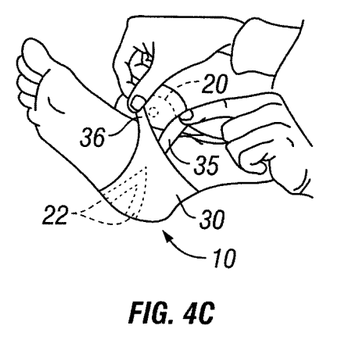
Figure 4D:
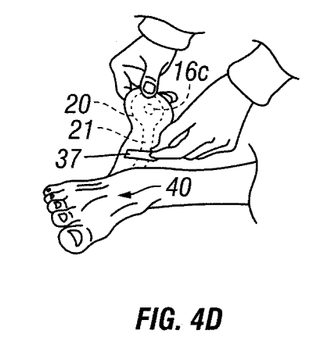
Figure 4E:
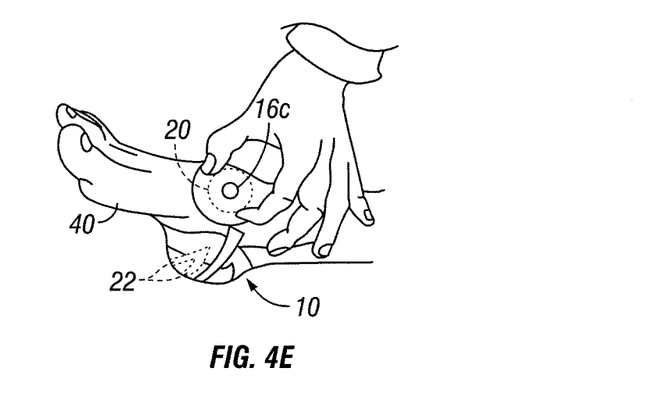
Figure 4F:
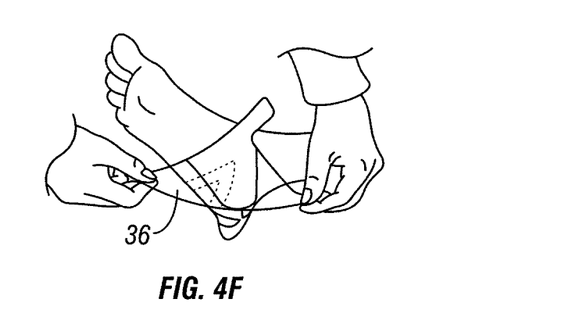
Figure 4G:
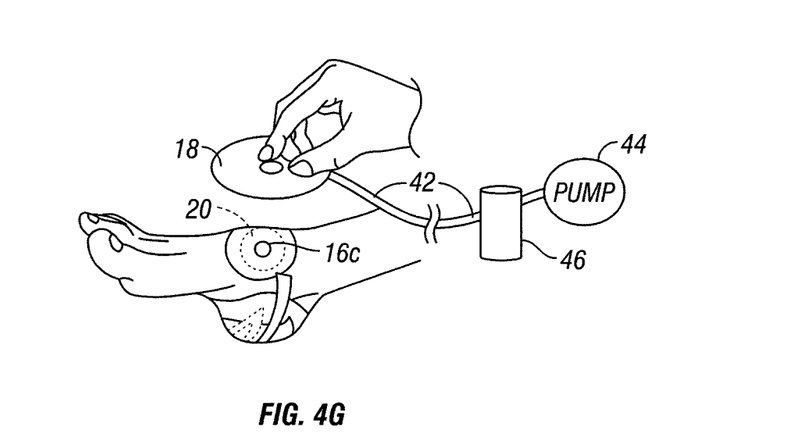

In practice, the contoured pad 26 is trimmed to the areal dimensions of the wound and is placed in the wound, which may be on the heel of a foot, and between the wound and the fluid manifold 14, as illustrated in FIGS. 4A-4G. The pad 26 may be secured to the wound site by an adhesive strip 28, as shown in FIG. 4A, or by other means known in the art. In the preferred embodiment, the adhesive strip is constructed of the same vapor permeable polyurethane material as the inner and outer drapes 16a and 16b of the occlusive wrapping 10 having an adhesive coated on one side for securing the strip to the pad 26 and the intact skin surrounding the wound.

Figure 5:
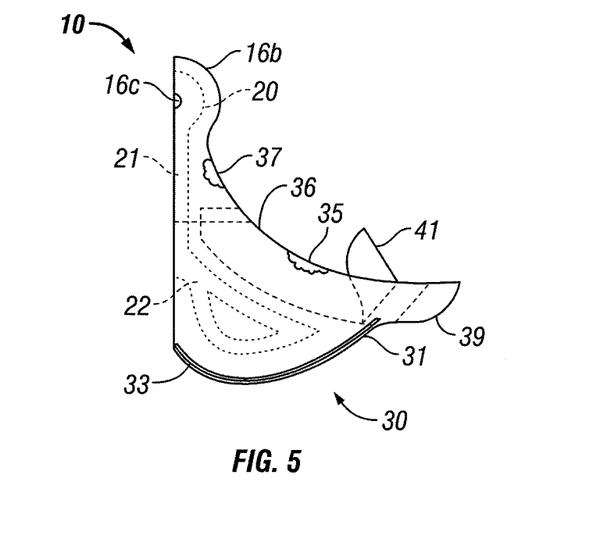
FIG. 5 is an orthogonal side view of the occlusive wrapping of FIG. 1B folded along its center line.

The occlusive wrapping 10 forms a pouch 30 when it is folded along its centerline and the lower edges 31 are bonded together at 33 as shown in FIG. 5. In practice, the pouch 30 is placed over the wound and contoured pad 26, as illustrated in FIGS. 4B and 4C. A fingerhold 39 is provided as an extension of protective liner 36 to facilitate grasping the pouch 30 and holding it in place as the removable liner components 35 are removed to expose adhesive backing on outer drape 16b. The edges 32a and 32b (shown in FIG. 4B) of the pouch 30 are brought into contact with the intact skin surrounding the wound by means of this adhesive backing. A removable liner 35 (visible through the partial section of protective liner 36) is pulled off, for example, starting at finger tab extension 41 of removable liner 35 (shown bent back for grasping in FIG. 5), exposing the adhesive, as shown in FIG. 4C. The removable liners 35 may be statically adhered to the adhesive backing on outer drape 16b to protect the adhesive during handling.

As illustrated in FIGS. 4D and 4E, a second removable liner 37 is adhered to the wound facing inner drape 16a to protect the adhesive on the wound facing inner drape 16a. The liner 37 is removed prior to adhesion of the wound facing inner drape 16a to a region 40 of intact skin away from the wound site, so as to help prevent dislodgement of the fluid communication port 18 (shown in FIG. 4G) during movement of the patient. Protective liner 36 in a preferred embodiment, is overlaid on the outer drape 16b (as illustrated in FIG. 1), so as to provide partial rigidity to the occlusive wrapping 10 and its fluid manifold 14 during handling. The liner 36 is removed after securing the pouch 30 to the wound site, as shown in FIG. 4F.

Reference is finally made to FIG. 4G which shows how a fluid communication port 18 is positioned over the receiving site 20, and is secured in place also by means of an adhesive contact surface on the communication port 18. As known in the art of negative pressure wound therapy, a fluid communication means 42, such as a flexible silicone tube, communicates negative pressure to the wound from a negative pressure source 44, such as a portable pump. A collection canister 46 is positioned in line between the negative pressure source 44 and the fluid communication means 42 to collect any exudates that may be drawn from the wound.

While the invention has been described herein with reference to certain preferred embodiments, theses embodiments have been presented by way of example only, and not to limit the scope of the invention. Many other variations are possible, which would be obvious to one skilled in the art. Accordingly, the scope of the invention should be identified only in accordance with the claims that follow.

What is claimed is:

1. A wound dressing for use under negative pressure, the wound dressing comprising:
   a fluid manifold having a receiving site and fluid communicator arms extending from the receiving site;
   a drape formed from an occlusive material and having an inner drape and an outer drape enclosing the fluid manifold, and an aperture formed on the outer drape that is substantially aligned with the receiving site, and wherein the inner drape includes a plurality of fenestrations in a wound contact region substantially aligned with the fluid communicator arms; and
   further comprising an extension region interposed between the receiving site and fluid communicator arms.

2. The wound dressing of claim 1, wherein the drape further comprises lower edges bonded together to form a pouch, and further comprising a porous pad positioned in the pouch.

3. The wound dressing of claim 2, wherein the porous pad comprises a concave porous pad formed from polyurethane.

4. The wound dressing of claim 1, wherein said fluid communicator arms terminate in contiguous loops.

5. A wound dressing for use under negative pressure, comprising:
   a concave porous pad adapted for placement on a wound;
   a fluid manifold having a receiving site and fluid communicator arms extending from the receiving site;
   a clear drape formed from an occlusive material and adapted for positioning over and around the concave porous pad, wherein said clear drape encloses said fluid manifold, an adhesive on at least an edge of said clear drape for sealing said at least a portion of said clear drape to an area surrounding the wound, and a plurality of fenestrations formed on the clear drape; and
   wherein said fluid communicator arms terminate in loops to allow viewing of the area around the wound through the clear drape.

6. The wound dressing of claim 5, wherein said clear drape is comprised of a wound faceable layer and an outer layer.

7. The wound dressing of claim 6, wherein said plurality of fenestrations are formed on the wound faceable layer for communicating fluid from the wound to said fluid manifold.

8. A wound dressing for use under negative pressure, comprising:
   a concave porous pad adapted for placement in a wound;
   a wrapping adapted for positioning over and around the concave porous pad, wherein said wrapping comprises a fluid manifold, a clear drape formed from an occlusive material and enclosing said fluid manifold, and an adhesive on at least an edge of said drape for sealing said wrapping to an area surrounding the wound;
   said fluid manifold comprising a receiving site, an extension region, and a fluid communicator arm, said receiving site distal to and in flow communication with said fluid communicator arm through said extension region, and wherein said fluid communicator arm is comprised of a plurality of contiguous loops to allow viewing of the area around the wound through the clear drape;
   wherein said clear drape is comprised of a wound faceable layer and an outer layer;
   wherein said wound faceable layer is fenestrated for communicating fluid from the wound to said fluid manifold; and
   wherein the wrapping further comprises lower edges bonded together to form a pouch.

\* \* \* \* \*